(12) United States Patent
Liu et al.

(10) Patent No.: US 9,644,031 B2
(45) Date of Patent: May 9, 2017

(54) EPIDERMAL GROWTH FACTOR RECEPTOR ANTIBODY

(71) Applicants: GENRIX (SHANGHAI) BIOPHARMACERTICAL CO., LTD., Shanghai (CN); BIOEX THERAPEUTICS INC., Shanghai (CN)

(72) Inventors: Jie Liu, Shandong (CN); Zhuobing Zhang, Shanghai (CN); Jikuan Shan, Shanghai (CN); Wei Suo, Shanghai (CN)

(73) Assignees: GENRIX (SHANGHAI) BIOPHARMACERTICAL CO., LTD., Shanghai (CN); BIOEX THERAPEUTICS INC., Shanghai (CN)

( * ) Notice: Subject to any disclaimer, the term of this patent is extended or adjusted under 35 U.S.C. 154(b) by 0 days.

(21) Appl. No.: 14/876,053

(22) Filed: Oct. 6, 2015

(65) Prior Publication Data
US 2016/0017045 A1    Jan. 21, 2016

Related U.S. Application Data

(63) Continuation of application No. PCT/CN2013/073811, filed on Apr. 7, 2013.

(51) Int. Cl.
*C07K 16/28* (2006.01)
*A61K 47/48* (2006.01)
*A61K 51/10* (2006.01)

(52) U.S. Cl.
CPC .... *C07K 16/2863* (2013.01); *A61K 47/48561* (2013.01); *A61K 51/1027* (2013.01); *C07K 2317/21* (2013.01); *C07K 2317/51* (2013.01); *C07K 2317/515* (2013.01); *C07K 2317/52* (2013.01); *C07K 2317/732* (2013.01)

(58) Field of Classification Search
CPC ............ C07K 16/2863; C07K 2317/51; C07K 2317/515; A61K 47/48561; A61K 51/1027
See application file for complete search history.

(56) References Cited

U.S. PATENT DOCUMENTS

| | | | |
|---|---|---|---|
| 7,649,083 B2 * | 1/2010 | Winston, Jr. ............ | C07K 16/22 530/387.1 |
| 8,586,714 B2 * | 11/2013 | Ghayur .................. | A61K 45/06 424/134.1 |
| 8,822,645 B2 * | 9/2014 | Ghayur .................. | C07K 16/22 424/130.1 |
| 9,029,508 B2 * | 5/2015 | Ghayur .................. | C07K 16/22 424/130.1 |
| 9,109,026 B2 * | 8/2015 | Ghayur .................. | C07K 16/18 |
| 2013/0330350 A1 * | 12/2013 | Dimasi .............. | C07K 16/2863 424/143.1 |

FOREIGN PATENT DOCUMENTS

| | | | | |
|---|---|---|---|---|
| CN | 103172741 | * | 6/2013 | ............ C07K 16/28 |
| WO | WO 02/100348 A2 | | 12/2002 | |
| WO | WO 2005/090407 A1 | | 9/2005 | |
| WO | WO 2011/028811 A2 | | 3/2011 | |
| WO | WO 2011/028811 A3 | | 3/2011 | |

OTHER PUBLICATIONS

International Search Report in International Application No. PCT/CN2013/073811, mailed Jan. 16, 2014 (12 pages).
Schneider-Merck, T. et al., "Human IgG2 Antibodies against Epidermal Growth Factor Receptor Effectively Trigger Antibody-Dependent Cellular Cytotoxicity but, in Contrast to IgG1, Only by Cells of Myeloid Lineage," *Journal of Immunology*, vol. 184, pp. 512-520 (2010).
Bleeker, W.K. et al., "Dual Mode of Action of a Human Anti-Epidermal Growth Factor receptor Monoclonal Antibody for Cancer Therapy," *J. Immunol.*, vol. 173, pp. 4699-4707 (2003).
Castillo, L. et al., "Pharmacological Background of EGFR Targeting," *Ann. Oncology*, vol. 15, pp. 1007-1012 (2004).
Jorissen, R.N. et al., "Epidermal Growth Factor Receptor: Mechanisms of Activation and Signalling," *Exp. Cell Res.*, vol. 284, pp. 31-53 (2003).
Mendelsohn, J. et al., "Status of Epidermal Growth Factor Receptor Antagonists in the Biology and Treatment of Cancer," *J. Clin. Oncology*, vol. 21, pp. 2787-2799 (2003).
Olayioye, M.A. et al., "The ErbB Signaling Network: receptor Heterodimerization in Development and Cancer," *The EMBO Journal*, vol. 19, pp. 3159-3167 (2000).
Patel, D. et al., "IgG Isotype, Glycosylation, and EGFR Expression Determine the Induction of Antibody-Dependent Cellular cytotoxicity in vitro by Cetuximab," *Human Antibodies*, vol. 19, pp. 89-99 (2010).
Steplewski, A. et al., "Biological Activity of Human-Mouse IgG1, IgG2, IgG3, and IgG4 Chimeric Monoclonal Antibodies with Antitumor Specificity," *Proc. Natl. Acad. Sci. USA*, vol. 85, pp. 4852-4856 (1988).
European Extended Search Report, dated Nov. 23, 2016, in corresponding European Application No. 13881974.3.
Rivera, F. et al., "Current Situation of Panitumumab, Matuzumab, Nimotuzumab and Zalutumumab," *Acta Oncologica*, vol. 47, pp. 9-10 (2008).
Kuenen, B. et al., "A Phase I Pharmacologic Study of Necitumumab (IMC-11F8), a Fully Human IgG1 Monoclonal Antibody Directed Against EGFR in Patients with Advanced Solid Malignancies," *Clinical Cancer Research*, vol. 16, No. 6, pp. 1915-1923 (2010).

* cited by examiner

*Primary Examiner* — Robert Landsman
(74) *Attorney, Agent, or Firm* — Bookoff McAndrews, PLLC

(57) ABSTRACT

Provided are an improved EGFR antibody or a functional segment thereof, comprising an engineered heavy chain and light chain. Specifically, the antibody is an engineered whole human-source monoclonal antibody. Also provided is a method for manufacturing said whole human-source antibody and usage of the antibody in the manufacture of medicines used for the treatment of tumors.

12 Claims, 5 Drawing Sheets

Gel confirmation of the PCR products

SEQUENCE LISTING

```
<160> NUMBER OF SEQ ID NOS: 43

<210> SEQ ID NO 1
<211> LENGTH: 449
<212> TYPE: PRT
<213> ORGANISM: Homo sapiens
```

<400> SEQUENCE: 1

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Val Ser Ser Gly
             20                  25                  30

Asp Tyr Tyr Trp Thr Trp Ile Arg Gln Ser Pro Gly Lys Gly Leu Glu
         35                  40                  45

Trp Ile Gly His Ile Tyr Tyr Ser Gly Asn Thr Asn Tyr Asn Pro Ser
 50                  55                  60

Leu Lys Ser Arg Leu Thr Ile Ser Ile Asp Thr Ser Lys Thr Gln Phe
 65                  70                  75                  80

Ser Leu Lys Leu Ser Ser Val Thr Ala Ala Asp Thr Ala Ile Tyr Tyr
                 85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
```

```
                    405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 2
<211> LENGTH: 449
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Val Ser Ser Gly
            20                  25                  30

Asp Tyr Tyr Trp Thr Trp Ile Arg Gln Ala Pro Gly Lys Gly Leu Glu
            35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Val Arg Asp Arg Val Thr Gly Ala Phe Asp Ile Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                    325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 3
<211> LENGTH: 214
<212> TYPE: PRT
<213> ORGANISM: Homo sapiens

<400> SEQUENCE: 3

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Asp Ala Ser Asn Leu Glu Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Phe Cys Gln His Phe Asp His Leu Pro Leu
                85                  90                  95
Ala Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 4
<211> LENGTH: 214
<212> TYPE: PRT
```

<213> ORGANISM: Homo sapiens

<400> SEQUENCE: 4

```
Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Asp Ala Ser Asn Leu Glu Thr Gly Val Pro Ser Arg Phe Ser Gly
50                  55                  60
Ser Gly Ser Gly Thr Asp Phe Thr Ile Thr Ile Ser Ser Leu Gln Pro
65                  70                  75                  80
Glu Asp Phe Ala Thr Tyr Phe Cys Gln His Phe Asp His Leu Pro Leu
                85                  90                  95
Ala Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 5
<211> LENGTH: 119
<212> TYPE: PRT
<213> ORGANISM: Homo sapiens

<400> SEQUENCE: 5

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Val Ser Ser Gly
            20                  25                  30
Asp Tyr Tyr Trp Thr Trp Ile Arg Gln Ser Pro Gly Lys Gly Leu Glu
        35                  40                  45
Trp Ile Gly His Ile Tyr Tyr Ser Gly Asn Thr Asn Tyr Asn Pro Ser
50                  55                  60
Leu Lys Ser Arg Leu Thr Ile Ser Ile Asp Thr Ser Lys Thr Gln Phe
65                  70                  75                  80
Ser Leu Lys Leu Ser Ser Val Thr Ala Ala Asp Thr Ala Ile Tyr Tyr
                85                  90                  95
Cys Val Arg Asp Arg Val Thr Gly Ala Phe Asp Ile Trp Gly Gln Gly
            100                 105                 110
Thr Met Val Thr Val Ser Ser
        115
```

```
<210> SEQ ID NO 6
<211> LENGTH: 119
<212> TYPE: PRT
<213> ORGANISM: Homo sapiens

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Val Ser Ser Gly
            20                  25                  30

Asp Tyr Tyr Trp Thr Trp Ile Arg Gln Ala Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Val Arg Asp Arg Val Thr Gly Ala Phe Asp Ile Trp Gly Gln Gly
            100                 105                 110

Thr Leu Val Thr Val Ser Ser
        115

<210> SEQ ID NO 7
<211> LENGTH: 326
<212> TYPE: PRT
<213> ORGANISM: Homo sapiens

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
```

```
                210                 215                 220
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 8
<211> LENGTH: 330
<212> TYPE: PRT
<213> ORGANISM: Homo sapiens

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

-continued

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Phe Asp His Leu Pro Leu
                85                  90                  95

Ala Phe Gly Gln Gly Thr Lys Val Glu Ile Lys
            100                 105

<210> SEQ ID NO 11
<211> LENGTH: 107
<212> TYPE: PRT
<213> ORGANISM: Homo sapiens
```

-continued

<400> SEQUENCE: 11

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 12
<211> LENGTH: 54
<212> TYPE: DNA
<213> ORGANISM: Artificial sequence
<220> FEATURE:
<223> OTHER INFORMATION: Oligonucleotide fragment of PCR primer

<400> SEQUENCE: 12
caggtgcagt tgcaggagag cggccctggc ctggtgaagc cctccgagac gttg         54

<210> SEQ ID NO 13
<211> LENGTH: 56
<212> TYPE: DNA
<213> ORGANISM: Artificial sequence
<220> FEATURE:
<223> OTHER INFORMATION: Oligonucleotide fragment of PCR primer

<400> SEQUENCE: 13
gcggcgacta ctactggacg tggatcaggc aaagccccgg caagggcctg gagtgg       56

<210> SEQ ID NO 14
<211> LENGTH: 58
<212> TYPE: DNA
<213> ORGANISM: Artificial sequence
<220> FEATURE:
<223> OTHER INFORMATION: Oligonucleotide fragment of PCR primer

<400> SEQUENCE: 14
tacaacccca gcctgaaatc caggttgacc atctccatcg acacgagcaa gacgcagt     58

<210> SEQ ID NO 15
<211> LENGTH: 57
<212> TYPE: DNA
<213> ORGANISM: Artificial sequence
<220> FEATURE:
<223> OTHER INFORMATION: Oligonucleotide fragment of PCR primer

<400> SEQUENCE: 15
acaccgccat ctattactgc gtgagggaca gggtgacagg cgccttcgac atctgct      57

<210> SEQ ID NO 16
<211> LENGTH: 54
<212> TYPE: DNA
<213> ORGANISM: Artificial sequence
<220> FEATURE:
<223> OTHER INFORMATION: Oligonucleotide fragment of PCR primer

<400> SEQUENCE: 16
tggatacgct gccgccgctc acggtacagg tcaggctcaa cgtctcggag ggct    54

<210> SEQ ID NO 17
<211> LENGTH: 55
<212> TYPE: DNA
<213> ORGANISM: Artificial sequence
<220> FEATURE:
<223> OTHER INFORMATION: Oligonucleotide fragment of PCR primer

<400> SEQUENCE: 17
gttcgtgttg cctgagtaat agatgtggcc gatccactcc aggcccttgc cgggg    55

<210> SEQ ID NO 18
<211> LENGTH: 55
<212> TYPE: DNA
<213> ORGANISM: Artificial sequence
<220> FEATURE:
<223> OTHER INFORMATION: Oligonucleotide fragment of PCR primer

<400> SEQUENCE: 18
agtcacgctg acagtttca ggctgaactg cgtcttgctc gtgtcgatgg agatg    55

<210> SEQ ID NO 19
<211> LENGTH: 55
<212> TYPE: DNA
<213> ORGANISM: Artificial sequence
<220> FEATURE:
<223> OTHER INFORMATION: Oligonucleotide fragment of PCR primer

<400> SEQUENCE: 19
gctggacacg gtcaccatcg ttccctggcc cagcagatgt cgaaggcgcc tgtca    55

<210> SEQ ID NO 20
<211> LENGTH: 55
<212> TYPE: DNA
<213> ORGANISM: Artificial sequence
<220> FEATURE:
<223> OTHER INFORMATION: Oligonucleotide fragment of PCR primer

<400> SEQUENCE: 20
gaggtgcagt tggtggagtc tgggggaggc ctggtgcagc ctggaggctc cctga    55

<210> SEQ ID NO 21
<211> LENGTH: 54
<212> TYPE: DNA
<213> ORGANISM: artificial sequence
<220> FEATURE:
<223> OTHER INFORMATION: Oligonucleotide fragment of PCR primer

<400> SEQUENCE: 21
tggcgattac tattggacct ggatcaggca ggctccaggg aagggcctgg agtg    54

<210> SEQ ID NO 22
<211> LENGTH: 54
<212> TYPE: DNA
<213> ORGANISM: artificial sequence
<220> FEATURE:
<223> OTHER INFORMATION: Oligonucleotide fragment of PCR primer

<400> SEQUENCE: 22
tataacccct ccctcaagag cagactgacc atctccagag acaacagcaa gaac    54

<210> SEQ ID NO 23
<211> LENGTH: 54

```
<212> TYPE: DNA
<213> ORGANISM: artificial sequence
<220> FEATURE:
<223> OTHER INFORMATION: Oligonucleotide fragment of PCR primer

<400> SEQUENCE: 23
acacggctgt gtattactgt gtgagagatc gagtgactgg tgcttttgac atct          54

<210> SEQ ID NO 24
<211> LENGTH: 54
<212> TYPE: DNA
<213> ORGANISM: artificial sequence
<220> FEATURE:
<223> OTHER INFORMATION: Oligonucleotide fragment of PCR primer

<400> SEQUENCE: 24
ctgctgacgg agcctccaga ggcagcacag gagagtctca gggagcctcc aggc          54

<210> SEQ ID NO 25
<211> LENGTH: 54
<212> TYPE: DNA
<213> ORGANISM: artificial sequence
<220> FEATURE:
<223> OTHER INFORMATION: Oligonucleotide fragment of PCR primer

<400> SEQUENCE: 25
gtgttcccac tgtaatagat gtggccgatc cactccaggc ccttccctgg agcc          54

<210> SEQ ID NO 26
<211> LENGTH: 53
<212> TYPE: DNA
<213> ORGANISM: artificial sequence
<220> FEATURE:
<223> OTHER INFORMATION: Oligonucleotide fragment of PCR primer

<400> SEQUENCE: 26
cctcggctcc aggctgttca tttgcaaata cagggtgttc ttgctgttgt ctc           53

<210> SEQ ID NO 27
<211> LENGTH: 54
<212> TYPE: DNA
<213> ORGANISM: artificial sequence
<220> FEATURE:
<223> OTHER INFORMATION: Oligonucleotide fragment of PCR primer

<400> SEQUENCE: 27
tgaggagacc gtgaccaggg ttccctggcc ccagatgtca aaagcaccag tcac          54

<210> SEQ ID NO 28
<211> LENGTH: 54
<212> TYPE: DNA
<213> ORGANISM: artificial sequence
<220> FEATURE:
<223> OTHER INFORMATION: Oligonucleotide fragment of PCR primer

<400> SEQUENCE: 28
gacatccaga tgactcagag ccccagttcc ctgagcgcct ctgtgggaga ccgg          54

<210> SEQ ID NO 29
<211> LENGTH: 54
<212> TYPE: DNA
<213> ORGANISM: artificial sequence
<220> FEATURE:
<223> OTHER INFORMATION: Oligonucleotide fragment of PCR primer

<400> SEQUENCE: 29
```
tacttgaact ggtatcaaca gaagcctgga aaggccccaa agctcctgat ctac        54

<210> SEQ ID NO 30
<211> LENGTH: 54
<212> TYPE: DNA
<213> ORGANISM: artificial sequence
<220> FEATURE:
<223> OTHER INFORMATION: Oligonucleotide fragment of PCR primer

<400> SEQUENCE: 30
aggttcagcg ggtccggaag cggcaccgac ttcacgttca ccatcagctc cctg        54

<210> SEQ ID NO 31
<211> LENGTH: 47
<212> TYPE: DNA
<213> ORGANISM: artificial sequence
<220> FEATURE:
<223> OTHER INFORMATION: Oligonucleotide fragment of PCR primer

<400> SEQUENCE: 31
atcacttgcc cctggcattc ggaggcggca caaaggtgga gattaag        47

<210> SEQ ID NO 32
<211> LENGTH: 53
<212> TYPE: DNA
<213> ORGANISM: artificial sequence
<220> FEATURE:
<223> OTHER INFORMATION: Oligonucleotide fragment of PCR primer

<400> SEQUENCE: 32
gttggaaatg tcctggcttg cctggcacgt aatggtcacc cggtctccca cag        53

<210> SEQ ID NO 33
<211> LENGTH: 53
<212> TYPE: DNA
<213> ORGANISM: artificial sequence
<220> FEATURE:
<223> OTHER INFORMATION: Oligonucleotide fragment of PCR primer

<400> SEQUENCE: 33
gctaggcacg cccgtctcca ggttggaagc gtcgtagatc aggagctttg ggg        53

<210> SEQ ID NO 34
<211> LENGTH: 53
<212> TYPE: DNA
<213> ORGANISM: artificial sequence
<220> FEATURE:
<223> OTHER INFORMATION: Oligonucleotide fragment of PCR primer

<400> SEQUENCE: 34
cgaagtgctg gcaaaaatac gtggcgatgt cctcaggttg cagggagctg atg        53

<210> SEQ ID NO 35
<211> LENGTH: 53
<212> TYPE: DNA
<213> ORGANISM: artificial sequence
<220> FEATURE:
<223> OTHER INFORMATION: Oligonucleotide fragment of PCR primer

<400> SEQUENCE: 35
agtgatctta atctccacct ttgtgccgcc tccgaatgcc aggggcaagt gat        53

<210> SEQ ID NO 36
<211> LENGTH: 54
<212> TYPE: DNA
<213> ORGANISM: artificial sequence -continued

```
<220> FEATURE:
<223> OTHER INFORMATION: Oligonucleotide fragment of PCR primer

<400> SEQUENCE: 36
gacatccaga tgacccagtc tccatcctcc ctgtctgcat ctgtaggaga caga         54

<210> SEQ ID NO 37
<211> LENGTH: 54
<212> TYPE: DNA
<213> ORGANISM: artificial sequence
<220> FEATURE:
<223> OTHER INFORMATION: Oligonucleotide fragment of PCR primer

<400> SEQUENCE: 37
tacttgaatt ggtatcagca gaaaccaggg aaagccccta agctcctgat ctat         54

<210> SEQ ID NO 38
<211> LENGTH: 54
<212> TYPE: DNA
<213> ORGANISM: artificial sequence
<220> FEATURE:
<223> OTHER INFORMATION: Oligonucleotide fragment of PCR primer

<400> SEQUENCE: 38
ggttcagtgg cagcggaagt gggacagatt tcactctcac catcagcagc ttgc         54

<210> SEQ ID NO 39
<211> LENGTH: 47
<212> TYPE: DNA
<213> ORGANISM: artificial sequence
<220> FEATURE:
<223> OTHER INFORMATION: Oligonucleotide fragment of PCR primer

<400> SEQUENCE: 39
accatctccc gctcgctttc ggacaaggaa cgaaggtgga aatcaaa              47

<210> SEQ ID NO 40
<211> LENGTH: 53
<212> TYPE: DNA
<213> ORGANISM: artificial sequence
<220> FEATURE:
<223> OTHER INFORMATION: Oligonucleotide fragment of PCR primer

<400> SEQUENCE: 40
gttgctgatg tcctggctcg cctggcaagt gatggtgact ctgtctccta cag          53

<210> SEQ ID NO 41
<211> LENGTH: 53
<212> TYPE: DNA
<213> ORGANISM: artificial sequence
<220> FEATURE:
<223> OTHER INFORMATION: Oligonucleotide fragment of PCR primer

<400> SEQUENCE: 41
tgatggcacc cctgtttcca aattggaggc atcatagatv aggagcttag ggg          53

<210> SEQ ID NO 42
<211> LENGTH: 53
<212> TYPE: DNA
<213> ORGANISM: artificial sequence
<220> FEATURE:
<223> OTHER INFORMATION: Oligonucleotide fragment of PCR primer

<400> SEQUENCE: 42
caaagtgttg acagaagtag gttgcaaaat cttvaggctg caagvtgctg atg          53
```

```
<210> SEQ ID NO 43
<211> LENGTH: 55
<212> TYPE: DNA
<213> ORGANISM: artificial sequence
<220> FEATURE:
<223> OTHER INFORMATION: Oligonucleotide fragment of PCR primer

<400> SEQUENCE: 43
tttgatttcc accttcgttc cttcgttcct tgtccgaaag cgagcgggag atggt         55
```

EPIDERMAL GROWTH FACTOR RECEPTOR ANTIBODY

CROSS-REFERENCE TO RELATED APPLICATIONS

This application is a continuation of International PCT Application No. PCT/CN2013/073811, filed on Apr. 7, 2013, which is incorporated by reference herein in its entirety.

SEQUENCE LISTING

This application contains a sequence listing, submitted electronically in ASCII format under the filename Sequence_listing.txt, which is incorporated by reference herein in its entirety. The ASCII copy of the sequence listing was created on Nov. 26, 2016, and is 27,313 bytes in size.

TECHNICAL FIELD

The present disclosure relates to novel epidermal growth factor receptor (EGFR) antibody or functional fragment thereof and use thereof. In particular, the present disclosure relates to fully human EGFR antibody or functional fragment thereof. The present disclosure also relates to a method of preparing said antibodies and said antibody in the manufacture of a medicament for treatment of a tumor.

BACKGROUND

Antibodies have been used to treat cancer and immunological or vascular disease. Antibody—medicament conjugates allow targeted delivery of the medicament moiety to the tumor and other diseased tissue, and systemic administration of unconjugated pharmaceutical agents may bring unbearable levels of toxicity to normal cells.

Basic unit of Natural antibodies is a monomer, which is composed of two identical heavy chains and two identical light chains connected by disulfide bond. There are at least five different types of heavy chains, i.e. γ, α, δ, μ and ε, which provide different effector functions. Heavy chains γ, α and δ have three constant domains ($C_H1$, $C_H2$ and $C_H3$), heavy chains μ and ε have four constant domains ($C_H1$, $C_H2$, $C_H3$ and $C_H4$). Each heavy chain also has a variable domain ($V_H$). There are at least two types of light chain, i.e., λ and κ, wherein each light chain comprises a constant domain ($C_L$) and a variable domain ($V_L$).

According to the amino acid sequence of the heavy chain constant domain, native human antibody can be classified into five categories: IgG IgA, IgM, IgD and IgE. Several categories of these categories can be further divided into subclasses or isotypes, such as IgG1, IgG2, IgG3, IgG4, IgA, or IgA2. Typical IgG molecule consists of two heavy chains γ and two identical light chains (λ or κ). Disulfide bonds link the light chain and the heavy chain therebetween, and link the heavy chains each other. The constant domain of the light chain pairs with the first constant domain of the heavy chain, the variable domain of the light chain ($V_L$) pairs with the variable domain of the heavy chain ($V_H$), thereby forms an antigen recognition site (agretope).

Variability of the variable domains ($V_L$ or $V_H$) in the whole domain is not evenly distributed, and is generally concentrated in three segments called hypervariable regions. The more conservative parts in the variable domains are called the framework regions (FR). Each variable domain of native heavy and light chains comprise four FRs, the FR mainly form β-sheet structures connected by three hypervariable regions, which form the connecting β-sheet structure, and in some cases form part of a ring of β-sheet structure. The hypervariable regions in each chain is close to each other through the FR, and form an antigen binding site of an antibody together with hypervariable regions in another chain. See Kabat et al., SEQUENCES OF PROTEINS OF IMMUNOLOGICAL INTEREST, 5th Ed. Public Health Service, National Institutes of Health, Bethesda, Md. (1991).

Epidermal growth factor receptor (EGFR, HER1, c-ErbB1) is a transmembrane glycoprotein composed of 1186 amino acid residues, with a molecular weight of 170 kD. EGFR has three parts: extracellular region, transmembrane region, and intracellular region (Jorissen R N, Walker F, Pouliot N, et al., Epidermal growth factor receptor: mechanisms of activation and signaling. Exp Cell Res, 2003; 284: 31-53). EGFR belongs to tyrosine kinase receptor subfamily type I (ErbB 1-4), having a tyrosine kinase activity. EGFR is stably expressed in many epithelial tissues, and mesenchymal and neurogenic tissues. EGFR are also highly expressed in solid tumors occurred in different organs, such as head and neck cancer, ovarian cancer, cervical cancer, bladder cancer and esophageal cancer, etc. (Mendelsohn J, Baselga J. Status of epidermal growth factor receptor antagonists in the biology and treatment of cancer. J Clin Oncol, 2003; 21: 2787-2799). Growth factors such as transforming growth factor α (TGFα) and epidermal growth factor (EGF) are ligands for EGFR. The combination of these ligands with EGFR results in dimerization of EGFR, which activates an intracellular protein tyrosine kinase activity of the receptor, the C-terminal phosphorylation of specific tyrosine residues to provide binding sites for the intracellular signal transduction factor, thereby initiating multiple signal transduction pathways such as Shc, Grb2, Ras/MAPK, PI 3K and JAKs/STATs (Mendelsohn J, Baselga J. Status of epidermal growth factor receptor antagonists in the biology and treatment of cancer. J Clin Oncol, 2003; 21: 2787-2799; and Olayioye M A, Neve R M, Lane H A, et al. The EerbB Signaling network: receptor heterodimerzat ion in development and cancer. The EMBO J, 2000; 19: 3159-3167). EGFR regulates growth and differentiation of normal cells, increases invasiveness of tumor cells, promotes angiogenesis, inhibits apoptosis of tumor cells through mediating these pathways. (Castillo L, Etienne-Grimaldi M C, Fischel J L, et al. Pharmacological background of EGFR targeting Ann Oncol, 2004; 15: 1007-1012). For the characteristics of EGFR such as highly expression in tumors and important roles in tumor cell growth and differentiation, EGFR become promising targets for cancer diagnosis and treatment.

In recent years, there is growing evidence proving that the epidermal growth factor receptor (EGFR) is relevant with the occurrence and development of many tumors. In a variety of solid tumors, EGFR expression rate in head and neck cancer is the highest up to 95%-100%. Colorectal cancer is the second, with the expression rate of 72%-89%. EGFR-positive tumors have features of high malignancy and strong invasion, and EGFR expression levels correlated with prognosis. Thus it also becomes an important target for the current molecularly targeted cancer therapy. There is some evidence to verify that HER1/EGFR is expressed abnormally in solid tumors, and its clinical manifestations is transfer, shortened survival, poor prognosis, and well tolerations to chemotherapy and hormone therapy. After blocking HER1/EGFR, tumor formation can be inhibited, while the above-mentioned condition can be improved.

EGFR targeted drugs currently used to treat cancer can be divided into two categories: EGFR monoclonal antibodies and small molecule tyrosine kinase antagonist compound. Tyrosine kinase antagonist is mainly a small molecule quinolone-based compounds, which can competitive inhibit binding of ATP and the intracellular tyrosine kinase domain of EGFR, thereby affect the phosphorylation of tyrosine residues and inhibit EGFR downstream signal transduction.

EGFR monoclonal antibody competitively binds EGFR with the endogenous ligand, and produces anti-tumor effects by inhibiting activation of tyrosine kinase and promoting internalization of the EGFR. Presently, there are three kinds of anti-EGFR monoclonal antibody available for market at home and abroad. Compared with other chemotherapy drugs, these antibodies have higher specificity, lower side effects and achieved good results in clinical therapy. EGFR is a mature target for antibody drug development. As one of the three most popular mature target for an anti-tumor antibody drug development (HER2, EGFR, VEGF), the status of targeted therapy medicaments relevant to EGFR target including antibodies medicaments in cancer therapy is very important. Because of the limitations of currently commercially available anti-EGFR antibody medicaments, research and development of novel anti-EGFR antibody medicaments with high efficiency and low toxicity has been the focus of international pharmaceutical industry research.

In vitro assays and in vivo animal tests showed, on one hand, EGFR monoclonal antibody Erbitux (cetuximab) binds with EGFR to block phosphorylation, inhibit ligand-activated EGFR tyrosine kinase activity, and promote endocytosis and degradation of EGFR, thereby inhibit tumor cell growth and induce apoptosis thereof; on the other hand, Erbitux (cetuximab) inhibit tumor cell growth by recruiting cells to the tumor surface, such as natural killer (NK) cells, etc., and further by cytotoxicity (Bleeker W K, Lammerts van Bueren J J, van Ojik H H, Gerritsen A F, Pluyter M, Houtkamp M, Halk E, Goldstein J, Schuurman J, van Dijk M A, van de Winkel J G; Parren P W. Dual mode of action of a human anti-epidermal growth factor receptor monoclonal antibody for cancer therapy. J Immunol 2004; 173: 4699-707).

In addition, it can be found from the summary of research results on antibody medicaments molecules and mechanism thereof during the therapy of diseases that, the therapeutic role of various anti-EGFR monoclonal antibodies in the body is not only relative with their affinity to EGFR, but also with the ADCC activity. (Patel D, Guo X, Ng S, Melchior M, Balderes P, Burtrum D, Persaud K, Luna X, Ludwig D L, Kang X. IgG isotype, glycosylation, and EGFR expression determine the induction of antibody-dependent cellular cytotoxicity in vitro by cetuximab. Hum Antibodies. 2010; 19: 89-99).

Furthermore, on the basis of without changing the three-dimensional structure of an antibody, antibody engineering technology can achieve conversion among IgG antibody subtypes (Z Steplewski, L K Sun, C W Shearman, J Ghrayeb, P Daddona, and H Koprowski. Biological Activity of Human-Mouse IgG1, IgG2, IgG3, and IgG4 chimeric monoclonal Antibodies with antitumor specificity. PNAS 1988; 85: 4852-4856).

Currently, with the development of technology, therapeutic monoclonal antibody is divided into three species: chimeric antibody sequences of about 70% human origin, humanized antibodies having 90-94% humanized sequences, as well as whole humanized antibody having 100% human sequence. The ratio of human sequence suggests the possibility of potential immunogenicity caused when the antibody is used for human treatment, therefore, the possibility of fully human antibody producing immunogenicity is lower than that of chimeric antibodies, and fully human antibody is better than chimeric antibody and humanized antibody when use as therapeutic medicaments.

ADCC (antibody-dependent cell-mediated cytotoxicity) refers to NK cells, macrophages and neutrophils which express IgG-Fc receptor, kill these target cells, by binding to Fc fragments of IgG antibody which have already been bound on surfaces of target cells such as virus-infected cells and tumor cells. IgG antibody can mediate ADCC function of these cells, wherein NK cells are major cells to show ADCC. In the occurrence of antibody-mediated ADCC action, the antibody can only specifically bind to the corresponding epitope on the target cells, effector cells such as NK cells can kill any target cells bound with the antibodies, so the binding of antibodies to antigens on the target cells is specific, while cytotoxicity to target cells by NK cells and other cells is non-specific.

Several anti-EGFR monoclonal antibody drugs already on the market still have many deficiencies. For example, Erbitux is a human chimeric IgG1 antibody, which has a considerable degree of immunogenicity, prone to human anti-mouse antibody response, worse side effects, thus affecting the efficacy thereof. Panitumumabhas a fully human IgG2 subtype, but it lacks of ADCC-relative biological activity, relies solely on blocking the EGFR signaling pathway to inhibit tumor growth, without another ADCC mechanism on inhibition of tumor, and thus the anti-tumor effect thereof is weak.

Accordingly, there remains a need for improved anti-EGFR antibodies to inhibit tumor. The present inventors have surprisingly found that by use of antibody engineering technology platform, panitumumab is changed from IgG2 subtype to IgG1 subtype, a fully human anti-EGFR antibody molecule with new sequence is formed, and the antibody molecule has the same target-binding characteristics with panitumumab, and because of different antibodies subtypes, the antibody molecule has a stronger ADCC biological activity, and a stronger anti-tumor effect compared with panitumumab. In addition, since the antibody is a fully human antibody molecule, which has a lower immunogenicity than that of the chimeric antibody Erbitux, it has lower potential clinical side effects. Thus, antibodies of the present disclosure brings together the advantages of antibodies known in the prior art and obtain unexpected technical effect.

SUMMARY OF THE PRESENT DISCLOSURE

Generally, the present disclosure provides a novel anti-EGFR antibody or functional fragment thereof, which on the one hand to reduce the side effects of the immunogenicity of chimeric antibodies, on the other hand by changing subtype of IgG antibody, to improve tumor suppression effect of the antibody.

Prior to the present disclosure, it has never been achieved as an anti-EGFR antibody gathering with various advantages of the prior art antibodies products. That is to say, it has never been able to obtain a fully human antibody with both a high level of binding EGFR and ADCC activity. The present inventors have unexpectedly achieve an anti-EFGR antibody bearing various advantages of the prior art antibodies through a reconstruction of heavy and light chains of panitumumab, in particular by changing subtype of panitumumab, for example by replacing antibody heavy chain IgG2 constant region with IgG1 constant region, optionally by further optimizing the framework region of the heavy chain and/or the light chain variable region. In some preferred embodiments, the present disclosure provides an antibody with subtype conversions (such as converting from IgG2 to IgG1). In other preferred embodiments, the present disclosure also provides antibodies with optimized framework regions of the heavy chain and/or the light chain variable region.

In one aspect, the present disclosure provides an antibody capable of binding to EGFR or functional fragment thereof comprising a heavy chain and a light chain, wherein (i) the heavy chain comprises a heavy chain variable region and a heavy chain constant region, wherein the heavy chain variable region has an amino acid sequence as shown in SEQ ID NO: 5 or SEQ ID NO: 6, and the heavy chain constant region is sequence of heavy chain constant region of human IgG1; and (ii) the light chain comprises a light chain variable region and a light chain constant region, wherein the light chain variable region having amino acid sequence as shown in SEQ ID NO: 9 or SEQ ID NO: 10.

In some embodiments, the antibody or functional fragment thereof is a fully human antibody or functional fragment thereof, preferably.

In other embodiments, the light chain constant region is human κlight chain constant region, e.g., having amino acid sequence as shown in SEQ ID NO: 11.

In still other embodiments, the heavy chain constant region has amino acid sequence as shown in SEQ ID NO: 8.

In still other embodiments, the heavy chain has amino acid sequence shown in SEQ ID NO: 1 or 2.

In still other embodiments, the light chain has amino acid sequence shown in SEQ ID NO: 3 or 4.

In some embodiments, the antibody or functional fragment thereof has ADCC activity.

In other embodiments, the antibody or functional fragment thereof inhibits EGFR phosphorylation downstream.

In still other embodiments, the antibody or functional fragment thereof inhibits EGFR signal transduction.

In another aspect, the present disclosure provides a nucleic acid molecule encoding the antibody or functional fragment thereof according to the present disclosure. Preferably, the nucleic acid molecule encodes heavy chain and light chain of the antibody or functional fragments of the present disclosure. In particular, the nucleic acid molecule is an isolated nucleic acid molecule.

In yet another aspect, the present disclosure provides a combination of nucleic acid molecules, comprising: a nucleic acid molecular encoding light chain of the antibody or functional fragments thereof according to any one of preceding claims, and a nucleic acid molecular encoding heavy chain of the antibody or functional fragment thereof according to any one of preceding claims. In particular, the combination of nucleic acid molecules is a combination of isolated nucleic acid molecules.

In yet another aspect, the present disclosure provides an immunoconjugate, comprising the antibody or functional fragment thereof according to the present disclosure conjugated with a therapeutic agent. In certain embodiments, the therapeutic agent is a toxin, a radioisotope, a medicament or a cytotoxin.

In yet another aspect, the present disclosure provides a pharmaceutical composition comprising the antibody or functional fragment thereof according to the present disclosure and/or immunoconjugate according to the present disclosure, and a pharmaceutically acceptable carrier.

In some aspects, the present disclosure provides a method of treating or preventing abnormal expression of EGFR-related diseases or disorders, including administering to a subject the antibody or functional fragment thereof, the immunoconjugate or pharmaceutical composition according to the present disclosure. In some embodiments, the disease or disorder is a tumor-related disease. Preferably, the tumor-related disease is selected from gastric cancer, esophageal cancer, pancreatic cancer, lung cancer, ovarian cancer, colon cancer, liver cancer, head and neck cancer and bladder cancer.

In further aspects, the present disclosure provides methods of inhibiting downstream phosphorylation of EGFR in a subject, signal transduction inhibition of EGFR and/or improving ADCC, the method comprising administering to a subject the antibody or functional fragment thereof, the immunoconjugate or pharmaceutical composition according to the present disclosure.

In other aspects, the present disclosure provides use of the antibody or functional fragment thereof, the nucleic acid molecule, the combination of nucleic acid molecules, the immunoconjugate or pharmaceutical composition according to the present disclosure in manufacture of medicaments for treatment or prevention of diseases or disorders related to abnormal expression of EGFR.

In further aspects, the present disclosure provides use of the antibody or functional fragment thereof according to the present disclosure, the nucleic acid molecule, the combination of nucleic acid molecules, the immunoconjugate or pharmaceutical composition in manufacture of medicaments for inhibiting the downstream phosphorylation of EGFR, inhibiting EGFR signal transduction and/or improving ADCC in a subject.

In further aspects, the present disclosure provides an antibody or functional fragment thereof, a nucleic acid molecule, a combination of nucleic acid molecules, immunoconjugate or pharmaceutical composition for the treatment or prevention of diseases or disorders related to abnormal expression of EGFR, or inhibition of downstream phosphorylation of EGFR, inhibition of EGFR signal transduction and/or improving ADCC in a subject.

In certain embodiments, the antibody or functional fragment thereof according to the present disclosure is isolated.

The present disclosure also provides a method for preparing the fully human antibody and functional fragment thereof, the method comprising the steps of:

1) Designing corresponding DNA sequence according to the antibody sequence of SEQ ID No.: 1-4;

2) synthesizing DNA sequences, it can be carried out by dividing the sequences into several pieces to be synthesized respectively and then connecting them to a complete fragments; or by synthesizing through PCR process by use of different primers;

3) the synthetic antibody DNA fragments are cloned into an expression plasmid;

4) the expression plasmid is transfected into a host cell;

5) the transfected host cells are cultured to obtain a supernatant of cell culture, and the desired antibody is obtained by purification.

DETAILED DESCRIPTION

Definitions

Figure 1:
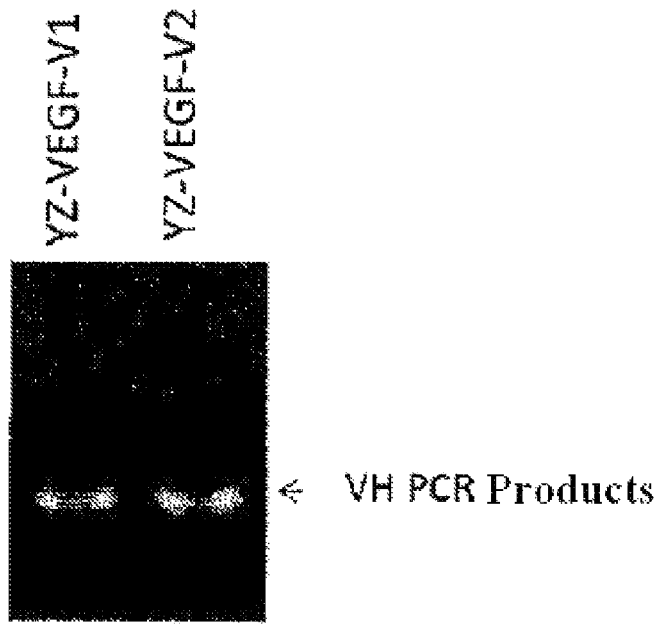
FIG. 1 shows the results of PCR product to identify sequences of the heavy and light chain variable region.
Figure 1:
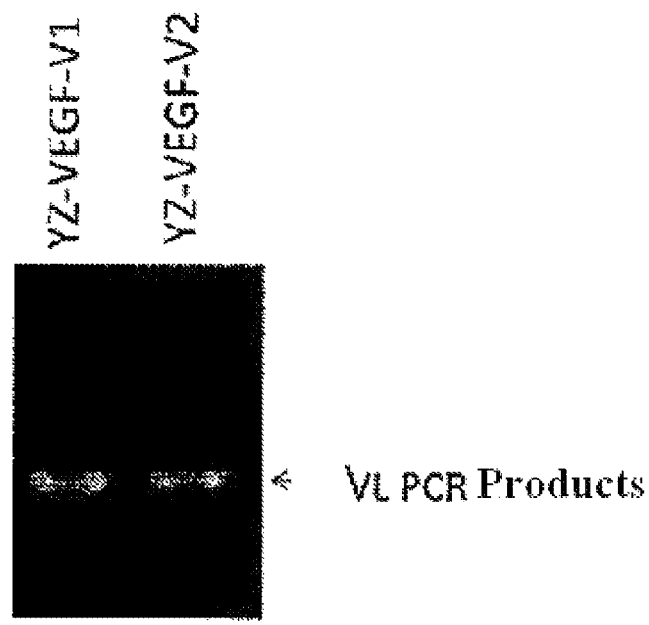

Unless otherwise defined, all technical and scientific terms used herein have the same meaning to the understanding of those of ordinary skilled in the art. Regarding the definitions and terminology in the art, professionals may refer to Current Protocols in Molecular Biology (Ausubel) for details. The abbreviations of amino acid residues used herein are the standard 3-letter and/or 1-letter code for one of the 20 commonly used L-amino acids.

Despite a broad scope of numerical ranges and parameters approximations is shown in the present disclosure, in specific embodiments and examples they are described as accurate as possible. However, any value must have some error, which is resulted from standard deviation in their respective measurement. In addition, all ranges disclosed herein should be understood to encompass any and all sub-ranges subsumed therein. For example, the scope of "1-10" described should be considered to comprise any and all sub-ranges between minimum 1 and maximum 10 (including the end point), that is, all sub-ranges starting with the minimum value of 1 or more, for example from 1 to 6.1, and sub-ranges ending with the maximum value of 10 or less, for example from 5.5 to 10. In addition, any references called "incorporated herein" should be understood to be incorporated in its entirety.

It should also be noted that, as used in this specification, the singular form of an object should include the plural form of the same, unless clearly and expressly limited to one object referred to. The term "or" and the term "and/or" are used interchangeably, unless the context clearly dictates otherwise.

The terms "pharmaceutical composition" "combination drug" and "pharmaceutical combination" as used herein, are used interchangeably, which represents a combination of at least one medicament and optionally a pharmaceutically acceptable carrier or excipients. In certain embodiments, the pharmaceutical composition comprises those combinations separated in time and/or space, as long as they can work together to achieve the object of the present disclosure. For example, the ingredients contained in the pharmaceutical composition (e.g., antibodies, nucleic acid molecules, nucleic acid molecules combinations and/or immunoconjugate of the present disclosure) may be administered to a subject as a whole, or separately administered to a subject. When the ingredients contained in the pharmaceutical composition are separately administered to a subject, the ingredients may be simultaneously or sequentially administered to a subject. Preferably, the pharmaceutically acceptable carrier may be water, a buffer aqueous solution and isotonic saline solution such as PBS (phosphate buffered saline), dextrose, mannitol, dextrose, lactose, starch, magnesium stearate, cellulose, magnesium carbonate, 0.3% glycerol, hyaluronic acid, ethanol, or polyalkylene glycols such as polyethylene glycol, triglycerides and the like. The type of pharmaceutically acceptable carrier used therein depends on the condition of whether it is used for oral, nasal, intradermal, subcutaneous, intramuscular, or intravenous administration of the composition according to the present disclosure, whether formulated. The composition according to the present disclosure may contain wetting agents, emulsifying agents or buffer substances as additives.

The pharmaceutical compositions, vaccine or pharmaceutical formulation of the present disclosure may be administered by any suitable route, such as oral, nasal, intradermal, subcutaneous, intramuscular, or intravenous administration.

"Therapeutically effective amount" or "effective amount" as used herein refers to a dosage sufficient to show benefit to the subject being administered. The actual amount administered, and rate and time-course of administration will depend on the situation and the severity of the person being treated. Prescription (e.g., decisions on dosage etc.) for treatment is ultimately responsibility of general practitioners and other physicians and relies on them to make decisions, usually under the consideration of the disease being treated, condition of the individual patient, the site of delivery, the method of administration and other known factors for doctors.

The term used herein "abnormal expression of EGFR-related disease or disorder" is intended to mean those diseases of disorders caused by the abnormal expression of EGFR or with symptoms/characteristics of abnormal expression of EGFR, preferably the diseases or disorders include, but are not limited to cancer and/or tumors, such as stomach cancer, esophageal cancer, pancreatic cancer, lung cancer, ovarian cancer, colon cancer, liver cancer, head and neck cancer and bladder cancer.

The term "subject" as used herein refers to a mammal, such as humans, but also other animals, such as wild animals (such as herons, storks, cranes, etc.), livestock (such as ducks, geese, etc.) or experimental animals (such as apes, monkeys, rats, mice, rabbits, guinea pigs, marmots, ground squirrel, etc.).

As used herein, the term "functional fragment" refers to an antibody fragment especially, such as Fv, scFv (sc refers to a single chain), Fab, F (ab') 2, Fab', scFv-Fc fragments or diabodies, or any fragments that can increase the half-life thereof by chemical modification, or by incorporation in a liposome. The chemical modification may be those modification such as chemical modification of adding poly (alkylene) glycols such as polyethylene glycol ("pegylation, PEG-lated") (referred to as Fv-PEG, scFv-PEG, Fab-PEG; F(ab')2-PEG or pegylated fragments of Fab'-PEG) ("PEG" is polyethylene glycol), and said fragments have activity of binding EGFR. Preferably, said functional fragments will be constituted by or contain partial sequence of the heavy or light variable chain of the antibody they derived from. The partial sequence is sufficient to retain the same binding specificity as their source antibody and sufficient affinity for EGFR, preferably at least equal to 1/100 of the affinity of the source antibody, in a more preferred embodiment at least equal to 1/10. Such functional fragment will include at least five amino acids, preferably 10, 15, 25, 50 and 100 contiguous amino acids of the sequence of source antibody.

The following examples are provided to demonstrate and further explain some of the preferred embodiments and aspects, and should not be construed as limiting the scope thereof.

Example 1

Design and expression of YZ-EGFR V1 and YZ-EGFR V2 antibody sequences: The present disclosure may use the genetic engineering method well known to those skilled in the art to prepare the desired fully human antibodies. In the example, only a method of obtaining the antibody sample for analysis and test by transient expression in 293-F cells is described. However, those skilled in the art will understand that the desired antibody can also be prepared by bacterial, yeast, viruses, and other eukaryotic expression systems, wherein the most optimal preparation system is to prepare and produce the fully human antibodies by use of Chinese hamster ovary cells (CHO) stable cell lines.

1. The following is the sequence of panitumumab heavy chain variable region (SEQ ID No: 5), wherein the sequence of the framework region is underlined:

QVQLQESGPGLVKPSETLSLTCTVSGGSVSSGDYYWTWIRQSPGKGLEWI

GHIYYSGNTNYNPSLKSRLTISIDTSKTQFSLKLSSVTAADTATYYCVRD

RVTGAFDI WGQGTMVTVSS

The following is the sequence of IgG2 heavy chain constant region (SEQ ID No: 7)

ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVICVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

The following is the sequence of IgG1 heavy chain constant region (SEQ ID No: 8):

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

YongZhuo-EGFR antibody-1 (YZ-EGFR v1) heavy chain sequence (SEQ ID No: 1) is formed by switching the original heavy chain IgG2 constant region sequence (SEQ ID NO:7) to IgG1 constant region sequences.

The non-optimized framework sequence in the original heavy chain variable region is changed to optimized framework sequence (SEQ ID No: 6):

EVQLVESGGG LVQPGGSLRL SCAASGGSVSSGDYYWTWIRQAPGKGLE

WIGHIYYSGNTNYNPSLKSRLTISRDNSKNTLYLQMNSLRAEDTAVYYCV

RDRVTGAFDIWGTLVTVSS

Then it is combined with the heavy chain IgG1 sequence to form a YongZhuo-EGFR antibody-2 (YZ-EGFR v2) heavy chain sequence (SEQ ID No: 2).

The following is the sequence of panitumumab light chain variable region (SEQ ID No: 9), wherein framework sequences are underlined:

DIQMTQSPSSLSASVGDRVTITCQASQDISNYLN WYQQKPGKAPKLLIY

DASNLETGVPSRFSGSGSGTDFTFTISSLQPEDIATYFCQHFDHLPLA

FGGGTKVEIK

The following is sequence of the light chain constant region CL (K) (SEQ ID No: 11):

RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

The sequence of panitumumab light chain variable region is combined with the light chain constant region CL (k) to form the sequence of YZ-EGFR v1 light chain (SEQ ID No: 3).

The non-optimized framework sequence in the original light chain variable region is changed to optimized framework sequence (SEQ ID No: 10):

DIQMTQSPSSLSASVGDRVTITCQASQDISNYLN WYQQKPGKAPKLLIY

DASNLETGVPSRFSGSGSGTDFTLTISSLQPEDFATYFCQHFDHLPLAFGQ

GTKVEIK

Then it is combined with the light chain constant region CL(K) sequence to form a
YZ-EGFR v2 light chain sequence (SEQ ID No: 4).

3. Preparation of Anti-EGFR antibody YZ-EGFR V1 and YZ-EGFR V2

This Example describes a method to obtain the antibody sample for analysis and test by transient expression in 293-F cells. The desired antibody could also be prepared by bacterial, yeast, viruses, and other eukaryotic expression systems, wherein the optimal system is to prepare and produce this fully human antibodies with Chinese hamster ovary cells (CHO) stable cell lines.

According to the sequences of heavy chain variable region and light chain variable region of antibodies YZ-EGFR V1 and YZ-EGFR V2, oligonucleotides fragments of PCR primers encoding the heavy and light chain variable region sequences were designed and synthesized. Adjacent oligonucleotide fragments have about 18 bp overlapped base pairs, and the length of PCR primer oligonucleotide fragments generally is about 54 bases. Equal amounts of each PCR primers fragments are mixed for the overlap extension PCR reaction.

Nucleic acid sequence of the primer fragments:

Each antibody sequence has eight (four pairs) primer sequences, each pair primer sequences are used for the preparation of mini-exon of YZ-EGFR V1 and YZ-EGFR V2 antibody VH and VL.

YZ-EGFR VI heavy chain (V1-HC):
Primer A 5' SEQ ID NO: 12:
CAGGTGCAGTTGCAGGAGAGCGGCCCTGGCCTGGTGAAGCCCTCCGAGAC
GTTG Primer B 5' SEQ ID NO: 13:
GCGGCGACTACTACTGGACGTGGATCAGGCAAAGCCCCGGCAAGGGCCTG
GAGTGG Primer C 5' SEQ ID NO: 14:
TACAACCCCAGCCTGAAATCCAGGTTGACCATCTCCATCGACACGAGCAA
GACGCAGT Primer D 5' SEQ ID NO: 15:
ACACCGCCATCTATTACTGCGTGAGGGACAGGGTGACAGGCGCCTTCGAC
ATCTGCT Primer A 3' SEQ ID NO: 16:
TGGATACGCTGCCGCCGCTCACGGTACAGGTCAGGCTCAACGTCTCGGAG
GGCT Primer B 3' SEQ ID NO: 17:
GTTCGTGTTGCCTGAGTAATAGATGTGGCCGATCCACTCCAGGCCCTTGC
CGGGG Primer C 3' SEQ ID NO: 18:
AGTCACGCTGGACAGTTTCAGGCTGAACTGCGTCTTGCTCGTGTCGATGG
AGATG Primer D 3' SEQ ID NO: 19:
GCTGGACACGGTCACCATCGTTCCCTGGCCCAGCAGATGTCGAAGGCGCC
TGTCA YZ-EGFR V2 heavy chain (V2-HC):
Primer A 5' SEQ ID NO: 20:
GAGGTGCAGTTGGTGGAGTCTGGGGGAGGCCTGGTGCAGCCTGGAGGCTC
CCTGA Primer B 5' SEQ ID NO: 21:
TGGCGATTACTATTGGACCTGGATCAGGCAGGCTCCAGGGAAGGGCCTGG
AGTG Primer C 5' SEQ ID NO: 22:
TATAACCCCTCCCTCAAGAGCAGACTGACCATCTCCAGAGACAACAGCAA
GAAC Primer D 5' SEQ ID NO: 23:
ACACGGCTGTGTATTACTGTGTGAGAGATCGAGTGACTGGTGCTTTTGAC
ATCT Primer A 3' SEQ ID NO: 24:
CTGCTGACGGAGCCTCCAGAGGCAGCACAGGAGAGTCTCAGGGAGCCTCC
AGGC Primer B 3' SEQ ID NO: 25:
GTGTTCCCACTGTAATAGATGTGGCCGATCCACTCCAGGCCCTTCCCTGG
AGCC Primer C 3' SEQ ID NO: 26:
CCTCGGCTCCAGGCTGTTCATTTGCAAATACAGGGTGTTCTTGCTGTTGT
CTC Primer D 3' SEQ ID NO: 27:
TGAGGAGACCGTGACCAGGGTTCCCTGGCCCCAGATGTCAAAAGCACCAG
TCAC YZ-EGFR V1 light chain (V1-LC):
Primer A 5' SEQ ID NO: 28:
GACATCCAGATGACTCAGAGCCCCAGTTCCCTGAGCGCCTCTGTGGGAGA
CCGG Primer B 5' SEQ ID NO: 29:
TACTTGAACTGGTATCAACAGAAGCCTGGAAAGGCCCCAAAGCTCCTGAT
CTAC Primer C 5' SEQ ID NO: 30:
AGGTTCAGCGGGTCCGGAAGCGGCACCGACTTCACGTTCACCATCAGCTC
CCTG Primer D 5' SEQ ID NO: 31:
ATCACTTGCCCCTGGCATTCGGAGGCGGCACAAAGGTGGAGATTAAG Primer A 3' SEQ ID NO: 32:
GTTGGAAATGTCCTGGCTTGCCTGGCACGTAATGGTCACCCGGTCTCCCA
CAG Primer B 3' SEQ ID NO: 33:
GCTAGGCACGCCCGTCTCCAGGTTGGAAGCGTCGTAGATCAGGAGCTTTG
GGG Primer C 3' SEQ ID NO: 34:
CGAAGTGCTGGCAAAAATACGTGGCGATGTCCTCAGGTTGCAGGGAGCTG
ATG Primer D 3' SEQ ID NO: 35:
AGTGATCTTAATCTCCACCTTTGTGCCGCCTCCGAATGCCAGGGGCAAGT
GAT YZ-EGFR V2 light chain (V2-LC):
Primer A 5' SEQ ID NO: 36:
GACATCCAGATGACCCAGTCTCCATCCTCCCTGTCTGCATCTGTAGGAGA
CAGA Primer B 5' SEQ ID NO: 37:
TACTTGAATTGGTATCAGCAGAAACCAGGGAAAGCCCCTAAGCTCCTGAT
CTAT -continued Primer C 5' SEQ ID NO: 38:
GGTTCAGTGGCAGCGGAAGTGGGACAGATTTCACTCTCACCATCAGCAGC

TTGC

Primer D 5' SEQ ID NO: 39:
ACCATCTCCCGCTCGCTTTCGGACAAGGAACGAAGGTGGAAATCAAA

Primer A 3' SEQ ID NO: 40:
GTTGCTGATGTCCTGGCTCGCCTGGCAAGTGATGGTGACTCTGTCTCCTA

CAG

Primer B 3' SEQ ID NO: 41:
TGATGGCACCCCTGTTTCCAAATTGGAGGCATCATAGATVAGGAGCTTAG

GGG

Primer C 3' SEQ ID NO: 42:
CAAAGTGTTGACAGAAGTAGGTTGCAAAATCTTVAGGCTGCAAGVTGCTG

ATG

Primer D 3' SEQ ID NO: 43:
TTTGATTTCCACCTTCGTTCCTTCGTTCCTTGTCCGAAAGCGAGCGGGAG

ATGGT

PCR reaction system: dNTPs 0.2 μM (final concentration); each PCR primer fragment: 1 μl; 10× buffer: 3 μl; cloned pfu (Invitrogen): 1 μl; water was added to 30 μl.

PCR reaction conditions: 94° C. initial denaturation for 3 minutes, setting 94° C. denaturation for 30 seconds, 56° C. anneal for 30 seconds, 72° C. extension for 1 minute, 30 cycles, and finally 72° C. further extension for 10 minutes.

The desired fragments are recovered and purified from PCR products after 1% agarose gel electrophoresis. After EcoRI digestion, the fragments are cloned into pCR-Bluntll-TOPO (Invitrogen) vector and then transformed into E. coli TOPO10 (Invitrogen) and screened on LB/Kanamycin plates. 10 white plaques was taken and inoculated in liquid LB culture medium containing Kanamycin. The plasmids are extracted with QIAGEN QIAquick PCR purification kit and sequences thereof are sequenced to confirm the heavy and light chain variable region sequence. The PCR products are shown in FIG. 1.

3. Construction of Expression Vectors

RNA were isolated from normal B Cells of human, to obtain human IgG1 heavy chain constant region Fc fragment and the light chain constant region κ fragment by PCR. The fragments are pre-constructed into pcDNA3.1 (Invitrogen) expression vector, transformed into DH5α bacterial cells. After plasmid extraction and sequencing, the positive clones are determined. YZ-EGFR V1 and YZ-EGFR V2 heavy chain variable region are cut from the positive clones of pCR-Bluntll-TOPO by Eco47III/NheI (Invitrogen), and ligated into pcDNA3.1-Fc expression vector. YZ-EGFR V1 and YZ-EGFR V2 light chain variable region are cut from the positive clones of pCR-Bluntll-TOPO by the AscI/BsiWI (Invitrogen) and ligated into pcDNA3.1-κ expression vector. Again, after transformed into DH5a bacterial cells, plasmids extraction and sequencing, the positive clones are determined. Sequencing resulting are consistent with the records of the antibody.

4. Antibody Expression

Figure 2:
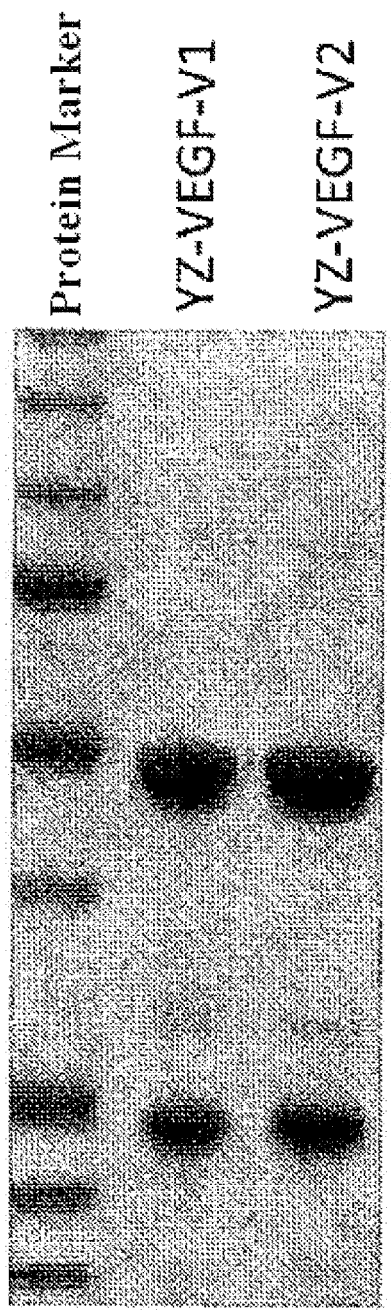
FIG. 2 shows the SDS-PAGE gel protein electrophoresis to determine the antibody.

For the expression of recombinant YZ-EGFR V1 and YZ-EGFR V2, YZ-EGFR V1 and YZ-EGFR V2 light chain and heavy chain plasmids were respectively transfected into 293-F cells (293fectin, available from Invitrogen). After the transfection cells cultured with FreeStyle 293 Expression medium (available from Invitrogen Corporation) in 100 ml flasks for five days, culturing supernatant was gathered by centrifugation and 0.22 μm membrane filtration. It is then purified using Protein A column (5 ml MabSelect preloaded column, available from GE Biosciences Inc.). Particular steps are as follows: after the column was equilibrated and buffered with 10 column volumes (10 CV) buffer (20 mM phosphate, 150 mM NaCl, pH7.0), the filtrated supernatant was loaded to the column with a flow rate of 2 ml/min. After rinsed using the equilibration buffer (20 mM phosphate buffer, 150 mM NaCl, pH7.0) for 10 column volumes (10 CV), the column was eluted with elution buffer (10 mM sodium citrate, pH3.5) for 5 column volumes. The eluted antibody was neutralized using 1 M TrisHCl, pH8.0 to pH6.5, and then the purified antibody was dialyzed to PBS. The antibody concentration was measured by ultraviolet method (280 nm wavelength), and purification rate thereof was measured by SDS-PAGE (FIG. 2). Cell culture supernatants were collected and purified by two Protein A purification. The purified antibodies after PBS dialysis underwent 0.22 μm membrane filtration for the following research work.

Example 2

ELISA Detection of Binding to EGFR

Materials:
YongZhuo-EGFR antibody-1 (YZ-EGFR V1); YongZhuo-EGFR antibody-2 (YZ-EGFR V2); Panitumumab (SY-puni, from Amgen company); EGFR-Fc (from Thermo Fisher company)

Methods: using a direct ELISA assay as follows:
1. ELISA plate was coated with 1 g/ml EGFR-Fc at 50 μl/hole, and laid down at 4° C. overnight (about 16 hours).
2. nonspecific sites on ELISA plate are blocked with TBS containing 1% BSA at 37° C. for 1 hour.
3. water was removed from ELISA plates, the plates were eluted with 2×TBST elution buffer.
4. a transfer tray was blocked with 1% BSA/TBS solution, 200 Whole, 37° C., 1 hour.
5. from the initial concentration of 3 μg/ml as the beginning, a series of antibodies are prepared in a transfer tray blocked with 1% BSA/TBS solution with a gradient of 1:3 dilution for test experiments. Each antibody was prepared with 8 concentrations gradient, and the final volume is 180 μl/hole.
6. in the EGFR-Fc coated ELISA plates (see step 1-3) antibody was added at different concentrations (as method in Step 5), 50 μl/hole, and incubated at 37° C. for 1 hour, the measurement of the sample was repeated once.
7. the water is removed from ELISA plate, and the plate was washed with 4×TBST.
8. donkey anti-human IgG-AP secondary antibody was diluted with 1% BSA/TBS at a ratio of 1:1000, 50 μl/hole, 37° C. for 1 hour.
9. ELISA plates were dried, and washed with 5×TBST.
10. 50 μl/hole PNPP buffer containing 0.1% PNPP substrate was added into the plate, and incubated at 37° C. for 15 minutes. 0.1% PNPP substrate in PNPP buffer was added at 50 μl/hole and incubated at 37° C. for 15 minutes.
11. 50 μl/hole of 1N sodium hydroxide was added to quench the reaction.
12. the absorbance was read at 405 nm by an enzyme-labelling measuring instrument.
13. the data was recorded and analyzed.

Figure 3:
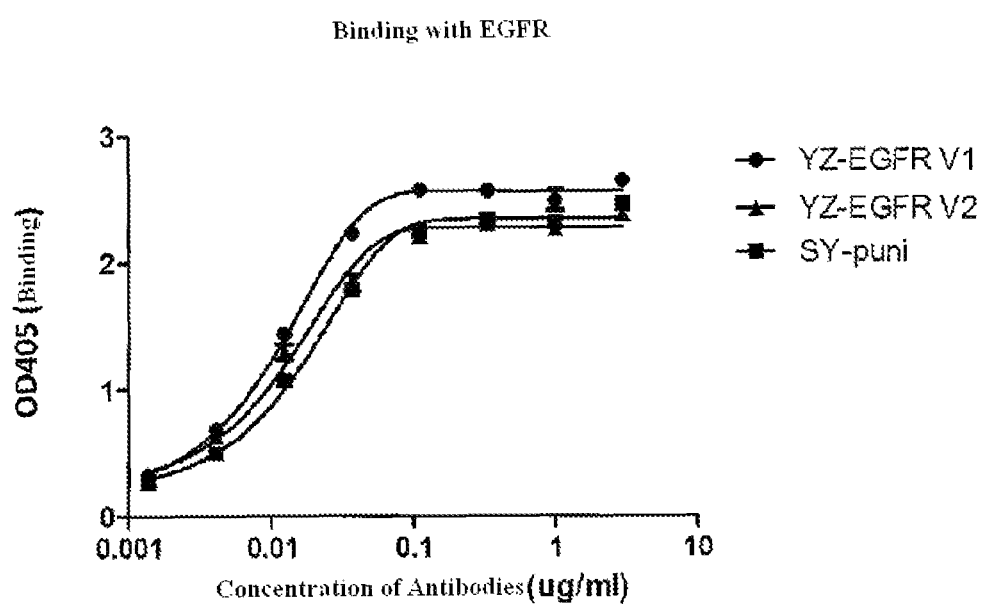
FIG. 3 shows a schematic view of an ELISA to assay binding between YongZhuo anti-EGFR antibody Cor called YZ-EGFR) and EGFR-Fc. The results showed that both YongZhuo-EGFR antibodies 1 and 2 have a consistent activity of binding EGFR directly, as same as panitumumab (SY-puni). It could demonstrate that YongZhuo anti-EGFR antibodies 1 and 2 could identify EGFR and have a similar affinity with panitumumab.

This assay results is shown in FIG. 3. FIG. 3 shows YongZhuo-EGFR antibodies 1 and 2 are same as panitumumab (SY-puni), have a consistent EGFR direct binding activity, which indicates that YongZhuo-EGFR antibody 1 and 2 can identify EGFR and affinity thereof is similar with that of panitumumab.

Example 3

In Vitro Assay of Anti-EGFR Antibody ADCC Reaction

Materials:

YongZhuo-EGFR antibody-1 (YZ-EGFR V1); YongZhuo-EGFR antibody-2 (YZ-EGFR V2); Panitumumab (SY-puni, from Amgen Inc.); Erbitux (cetuximab, from Imclone company); calcein-AM (Invitrogen Corporation); round-bottom 96-well plate (BD Science), peripheral blood mononuclear cells (PBMC) were purchased from AllCells Company (healthy donors).

Methods:

ADCC was detected with calcein-AM release method as follows

1. A431 (human epidermal cancer) cells was labeled with calcein-AM mark (15 μM/$10^6$ cells), and washed, in round-bottom 96-well plate with $5 \times 10^3$ cells/well, in triplicate.

2. anti-EGFR antibody (0.1 and 1 μg/ml) was added and pre-incubated with the labeled A431 at 4° C. for 30 minutes.

3. after Step 2, PBMC effector cells from healthy donors were added, final effect is: in a final volume of 200 μl/well, ratio of the target cells (labeled A431) and effector cells (PBMC) was 40:1.

4. The specific lysis ratio=(AFU average Experimental release−AFU average spontaneous release)/(AFU average maximum release−AFU average spontaneous release).

Figure 4:
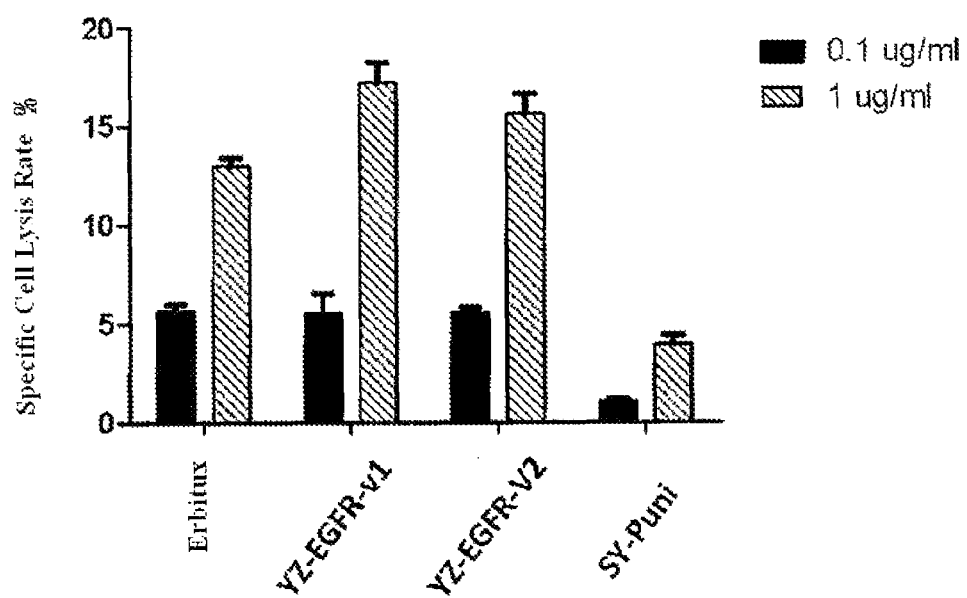
FIG. 4 shows a schematic diagram of an ADCC activity assay. The results showed that both YongZhuo anti-EGFR antibodies 1 and 2 have similar ADCC activity with Erbitux (cetuximab), which is significantly higher than that of panitumumab.

This assay results were shown in FIG. 4. The results in FIG. 4 showed that both YongZhuo-EGFR antibodies 1 and 2 have similar ADCC activity with Erbitux (cetuximab), and were significantly higher than panitumumab.

Example 4

EGFR Phosphorylation

Materials:

YongZhuo-EGFR antibody-1 (YZ-EGFR V1); YongZhuo-EGFR antibody-2 (YZ-EGFR V2); Panitumumab (SY-puni, from Amgen Inc.); Erbitux (cetuximab, from Imclone company); A431 cells (obtained from ATCC number: CRL-2592); recombinant human epidermal growth factor (from R & D company); cell lysis buffer (10×) (from Cell Signalling); BCA kit (from Pierce); anti-pEGFR (pY 1068) and the pan-anti-EGFR (from CST Corporation).

the assay steps are as follows:

1. Each 6-well plate was seeded $5 \times 10^5$ cells of A431 cells, and were incubated overnight with complete medium (DMEM+10% FBS).

2. the medium was replaced with 2 ml DMEM for culture, and cells lack of nutrition for 16-18 hours. Cells were starved for 16-18 hours with 2 ml DMEM.

3. the medium was replaced with 1 ml of preheated fresh medium (without 10% FBS) for culture and was incubated in incubator for 1-2 hours.

4. 30 minutes before stimulation with the recombinant EGF (epidermal growth factor), 10 g/ml anti-EGFR antibody (final concentration) was added to A431 cells.

5. cells were stimulated with EGF of final concentration of 0.5 ng/ml dissolved in PBS+0.01% BSA for 5 minutes.

6. Place the plate on ice, and wash it using a cold 1×PBS 3 times.

7. cells were added therein with 250 μl lysis solution for lysis and scraped off directly after lysis, vortexed or incubated on ice for 30 minutes.

8. cells were centrifuged at 14000 rpm, 4° C., for 15 min.

9. The protein was quantified using BCA kit.

10. Adjust the volume of the protein lysate solution with a suitable volume of loading buffer, and cook 5 minutes.

11. The 10-hole gel was poured out for Western Blot, 20 g lysate was loaded in each hole.

The experiment detects total EGFR and phosphorylated EGFR by Western Blot method. The lower part of FIG. 5, Total EGFR, shows the total EGFR content, including non-phosphorylated and phosphorylated EGFR. "pEGFR in the upper part of the figure shows the amount of EGFR after phosphorylation.

Figure 5:
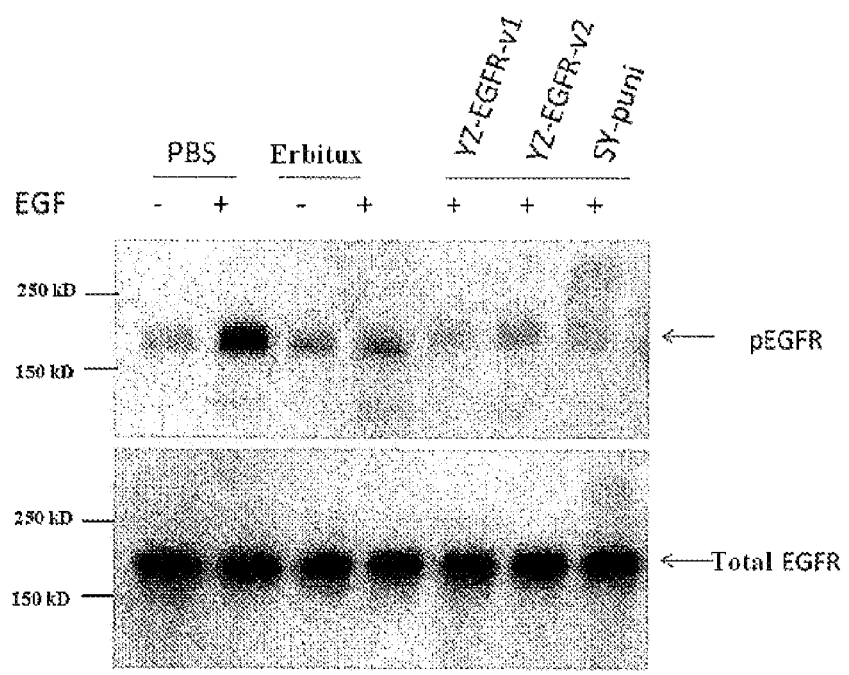
FIG. 5 shows a schematic view of inhibition effect of anti-EGFR antibody to the downstream phosphorylation of EGFR. In this assay, levels of total EGFR and that of EGFR after phosphorylation are detected by Western Blot. The lower part of the figure shows the total amount of EGFR with "Total EGFR", including post-phosphorylated EGFR and phosphorylated EGFR. "pEGFR" in the upper part of the figure shows the amount of EGFR after phosphorylation. Lane 1: molecular weight marker; 2: PBS plus EGF; 3: PBS without EGF (2, 3 for the PBS negative control); 4: Erbitux without EGF; 5: Erbitux plus EGF; 6: adding YongZhuo anti-EGFR antibody 1; 7: adding YongZhuo anti-EGFR antibody 2; 8: adding panitumumab (SY-puni). The results illustrate that under the condition of same total EGFR amount (below), all of YongZhuo anti-EGFR antibodies 1 and 2, Erbitux (erbitux) and panitumumab (SY-puni) can significantly inhibit EGFR downstream phosphorylation, and thus block signal pathway, which could further prove YongZhuo anti-EGFR antibodies 1 and 2 have the effects of binding EGFR, inhibition of downstream signal pathways and potential inhibition of tumor cells. Positive control of total antibodies and PBS negative control described the effectiveness of the experiment.

FIG. 5 illustrates that under the condition of same total EGFR amount (below), all of YongZhuo anti-EGFR antibodies 1 and 2, Erbitux (erbitux) and panitumumab (SY-puni) can significantly inhibit EGFR downstream phosphorylation, and thus block signal pathway, which could further prove YongZhuo anti-EGFR antibodies 1 and 2 have the effects of binding EGFR, inhibition of downstream signal pathways and inhibition of tumor cells. Positive control of total antibodies and PBS negative control described the effectiveness of the experiment.

Therefore, the above examples show, the present disclosure unexpectedly found that by panitumumab reconstruction, succeeded in obtaining an anti-EGFR antibody gathering with advantages of various antibodies products in the prior art.

The above description is only the preferred embodiments, which is provided by way of example only and not for limiting the essential features combination required for implementing the present disclosure. The title is not intended to be provided to limit the various embodiments of the present disclosure. Terms such as "including", "containing" and "comprising" is not intended to limiting. In addition, unless otherwise indicated, when there is no numeral it means conditions including the plural form, and "or", "or" means "and/or". Unless otherwise defined, all technical and scientific terms used herein have the same meaning to the understanding of those of ordinary skilled in the art.

All publications and patents mentioned in this application are incorporated herein by reference. Without departing from the scope and spirit of the present disclosure, various modifications and variations of the methods and compositions of the present disclosure are obvious for those skilled in the art. Although the present disclosure is described by the adoption of specific preferred embodiments, it should be understood that the claimed scope should not be unduly limited to such specific embodiments. In fact, those variants apparent for those skilled in the relevant art are intended to be included within the scope of the appended claims.

The invention claimed is:

1. An antibody or fragment thereof capable of binding to epidermal growth factor receptor (EGFR), the antibody or fragment thereof comprising a heavy chain and a light chain, wherein
   (i) the heavy chain comprises a heavy chain variable region and a heavy chain constant region, wherein the heavy chain variable region has the amino acid sequence of SEQ ID NO: 6, and the heavy chain constant region is a sequence of heavy chain constant region of human IgG1; and
   (ii) the light chain comprises a light chain variable region and a light chain constant region, wherein the light chain variable region has the amino acid sequence of SEQ ID NO: 9 or SEQ ID NO: 10;
   or
   (i) the heavy chain comprises a heavy chain variable region and a heavy chain constant region, wherein the heavy chain variable region has the amino acid sequence of SEQ ID NO: 5 or SEQ ID NO: 6, and the heavy chain constant region is a sequence of heavy chain constant region of human IgG1; and
   (ii) the light chain comprises a light chain variable region and a light chain constant region, wherein the light chain variable region has the amino acid sequence of SEQ ID NO: 10.

2. The antibody or fragment thereof according to claim 1, wherein the antibody or fragment thereof is a fully human antibody or fragment thereof.

3. The antibody or fragment thereof according to claim 1, wherein the light chain constant region is a human κ light chain constant region and/or the heavy chain constant region has the amino acid sequence of SEQ ID NO: 8.

4. The antibody or fragment thereof according to claim 3, wherein the light chain constant region has the amino acid sequence of SEQ ID NO: 11.

5. The antibody or fragment thereof according to claim 1, wherein the heavy chain has the amino acid sequence of SEQ ID NO: 1 or 2, and/or wherein the light chain has the amino acid sequence of SEQ ID NO: 3 or 4.

6. The antibody or fragment thereof according to claim 1, which has antibody-dependent cell-mediate cytotoxicity (ADCC) activity.

7. An immunoconjugate comprising an antibody or fragment thereof capable of binding to epidermal growth factor receptor (EGFR), the antibody or fragment thereof comprising a heavy chain and a light chain, wherein
   (i) the heavy chain comprises a heavy chain variable region and a heavy chain constant region, wherein the heavy chain variable region has the amino acid sequence of SEQ ID NO: 6, and the heavy chain constant region is a sequence of heavy chain constant region of human IgG1; and
   (ii) the light chain comprises a light chain variable region and a light chain constant region, wherein the light chain variable region has the amino acid sequence of SEQ ID NO: 9 or SEQ ID NO: 10;
   or
   (i) the heavy chain comprises a heavy chain variable region and a heavy chain constant region, wherein the heavy chain variable region has the amino acid sequence of SEQ ID NO: 5 or SEQ ID NO: 6, and the heavy chain constant region is a sequence of heavy chain constant region of human IgG1; and
   (ii) the light chain comprises a light chain variable region and a light chain constant region, wherein the light chain variable region has the amino acid sequence of SEQ ID NO: 10,
   wherein the antibody or fragment thereof is conjugated with a therapeutic agent.

8. The immunoconjugate according to claim 7, wherein the therapeutic agent is a toxin, a radioisotope, a medicament or a cytotoxin.

9. The immunoconjugate according to claim 7, wherein the antibody or fragment thereof is a fully human antibody or fragment thereof.

10. The immunoconjugate according to claim 7, wherein the light chain constant region is a human κ light chain constant region and/or the heavy chain constant region has the amino acid sequence as shown in of SEQ ID NO: 8.

11. The immunoconjugate according to claim 10, wherein the light chain constant region has the amino acid sequence of SEQ ID NO: 11.

12. The immunoconjugate according to claim 7, wherein the heavy chain has the amino acid sequence of SEQ ID NO: 1 or 2, and/or the light chain has the amino acid sequence of SEQ ID NO: 3 or 4.

* * * * *